United States Patent [19]

Mori

[11] Patent Number: 4,852,549
[45] Date of Patent: Aug. 1, 1989

[54] LIGHT RAY RADIATION DEVICE FOR ADMINISTERING ORAL MEDICAL TREATMENT TO DISEASED GUMS

[76] Inventor: Kei Mori, 3-16-3-501, Kaminoge, Setagaya-ku, Tokyo, Japan

[21] Appl. No.: 39,503

[22] Filed: Apr. 17, 1987

[30] Foreign Application Priority Data

Oct. 15, 1986 [JP] Japan ................................ 61-244875

[51] Int. Cl.$^4$ .......................... A61B 19/00; A61H 7/00
[52] U.S. Cl. .................................. 128/395; 128/62 A
[58] Field of Search .................. 128/1, 62 A; 433/25, 433/62, 30; 354/62; 250/475.2

[56] References Cited

U.S. PATENT DOCUMENTS

| | | | |
|---|---|---|---|
| 2,072,390 | 3/1937 | Hartingsvelt | 354/62 |
| 3,118,450 | 1/1964 | Freeman et al. | 433/25 |
| 3,379,192 | 4/1968 | Warren, Jr. | 128/62 A |
| 3,971,954 | 7/1976 | Kleinberg et al. | 250/475.2 |
| 4,164,940 | 8/1979 | Quinby | 433/25 |
| 4,324,546 | 4/1982 | Heitlinger et al. | 433/25 |
| 4,468,197 | 8/1984 | Provost | 433/30 |

Primary Examiner—Robert A. Hafer
Assistant Examiner—Michael Brown
Attorney, Agent, or Firm—Jordan and Hamburg

[57] ABSTRACT

A light rays radiation device for administering oral medical treatment to a person's gums that has a light ray radiating tool attachably and removably connected with the light ray emitting end-portion of an optical conductor cable through which the light rays corresponding to the visible light ray components of solar rays are transmitted to the light ray radiation tool. The light ray radiation tool has a mouthpiece having a transparent curved surface corresponding to the shape of the gums and a large number of optical fibers imbedded in the mouthpiece. The large number of optical fibers are constructed in such a manner that the end portions thereof are placed over the entire area of the transparent curved surface so as to be opposite the gum area and the other-side portions thereof are capable of being connected with the light ray emitting end portion of the optical conductor cable.

8 Claims, 3 Drawing Sheets

LIGHT RAY RADIATION DEVICE FOR ADMINISTERING ORAL MEDICAL TREATMENT TO DISEASED GUMS

BACKGROUND OF THE INVENTION

The present invention relates to a light ray radiation tool for the oral medical treatment of gums. The light rays that are free of harmful rays normally contained in solar rays are radiated effectively onto the person's gums for administering oral medical treatment.

In recent years, a large number of persons have been suffering from incurable diseases such as arthritis, neuralgia and rhumatism, or pain from injuries, or bond fractures, or ill-defined diseases. Furthermore, persons cannot prevent their skin from aging since the process is a gradual one. On the other hand, the present applicant has previously proposed to focus solar rays or artificial light rays by the use of lenses or the like, to guide the same into an optical conductor, and to transmit those solar rays or artificial light rays onto an optional desired place through the optical conductor. Those light rays transmitted in such a way are employed for use in illumination or for other like purposes, for example, to cultivate plants, chlorella, or the like. In the process thereof, it has been found that visible light rays not containing harmful ultraviolet rays and infrared rays, promote a healthy body reaction, and thereby improve a person's health and prevent the person's skin from the appearance of aging. Furthermore, those visible light rays help persons to recover from arthritis, neuralgia, bedsores, rheumatism, injuries from fire, skin disease, other injries, bone fractures, or the like, and of stopping the pain from those diseases.

In consideration of the above circumstances, the present applicant has previously proposed various light ray radiation devices for use in medical treatment capable of radiating light rays that correspond to the visible light ray components of solar rays not containing therein ultraviolet rays and infrared rays. The same can be used for promoting general health and for beauty treatment.

The present applicant has previously proposed a solar ray radiation device for use in medical treatment having an optical conductor cable and hood member installed at the light ray emitting end portion of the optical conductor cable. Solar rays or artificial light rays are guided into the optical conductor cable from the end portion thereof and transmitted therethrough. The light rays (the white-colored light rays) corresponding to the visible light ray components of solar rays are transmitted through the optical conductor cable in such a manner as was previously proposed in various ways by the present applicant. The semitransparent cylindrical hood member is installed at the light ray emitting end portion of the above-mentioned optical conductor cable.

At the time of administering medical treatment, a patient is laid on the medical treatment chair and the light rays consisting of the visible light ray components transmitted through the optical conductor cable are radiated onto the diseased part of the patient. The light rays to be radiated onto the diseased part of the patient are the ones corresponding to the visible light ray components of solar rays not containing ultraviolet rays and infrared rays as mentioned above. Thereby, it is possible to administer medical treatment without any harmful effects caused by ultraviolet or infrared rays.

However, the afore-mentioned light ray radiation device for use in medical treatment is employed mainly for the purpose of directing the light rays onto the surface of the patient's skin. In the case of focusing the light rays onto the gums or the like in order to treat pyorrhea, gingivitis, alveolaris, etc., it is impossible to radiate the light rays effectively onto the gums by the use of the above-mentioned conventional light ray radiation device. Consequently, the favorable effect of the medical treatment cannot be obtained.

SUMMARY OF THE INVENTION

It is an object of the present invention to provide a light ray radiation tool for use in the medical treatment of diseased gums.

It is another object of the present invention to provide a light ray radiation tool for radiating the light rays onto the gums effectively.

The above-mentioned features and other advantages of the present invention will be apparent from the following detailed description which goes with the accompanying drawings.

BRIEF DESCRIPTION OF THE DRAWINGS

FIG. 6c is a cross-sectional view taken along the line Y—Y of FIG. 6a.

DESCRIPTION OF THE PREFERRED EMBODIMENTS

Figure 1:
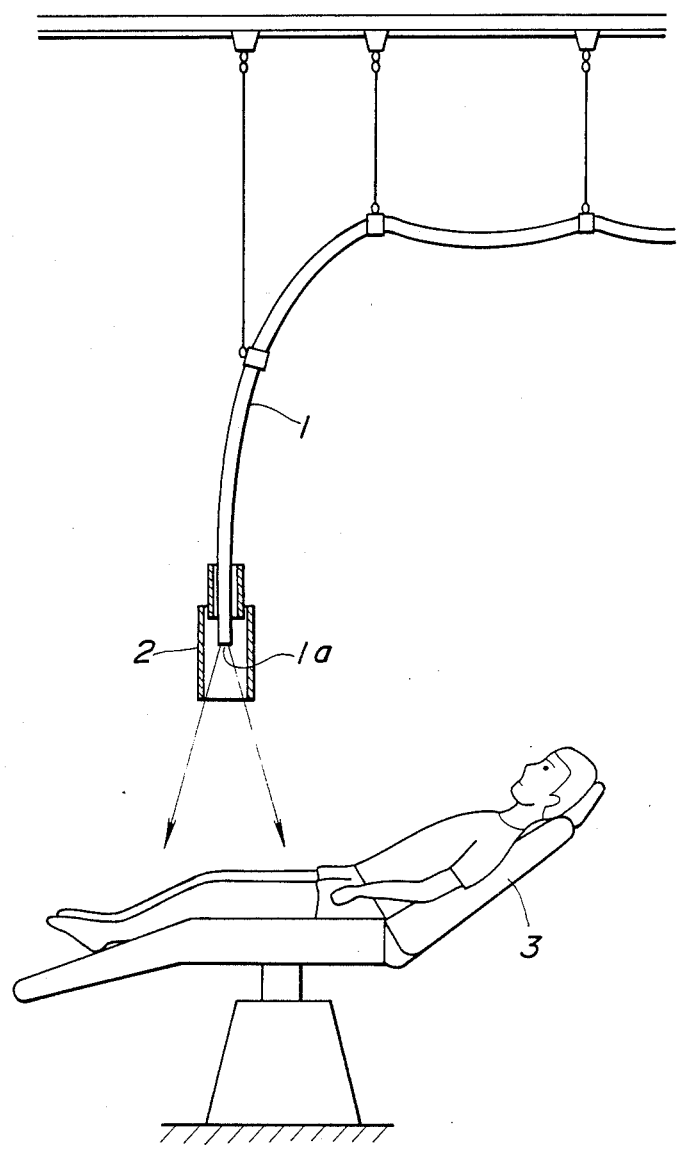
FIG. 1 is a construction view for explaining an embodiment of a light ray radiation device for use in medical treatment of the prior art.

FIG. 1 is a construction view for explaining an embodiment of a solar ray radiation device for use in medical treatment which has been previously proposed by the present applicant. In FIG. 1, 1 is an optical conductor cable. Solar rays or artificial light rays are guided into the optical conductor cable 1 from the end portion thereof (not shown) and transmitted therethrough. The light rays (the white-colored light rays) corresponding to the visible light ray components of solar rays are transmitted through the optical conductor cable 1 in such a manner as was previously proposed in various ways by the present applicant. In the same figure, 2 is a semitransparent cylindrical hood member installed at the light ray emitting end portion 1a of the above-mentioned optical conductor cable 1, and 3 is a medical treatment chair.

At the time of administering medical treatment, a patient is laid on the medical treatment chair and the light rays consisting of the visible light ray components transmitted through the optical conductor cable 1 are radiated onto the diseased part of the patient as mentioned before. The light rays to be radiated onto the diseased part of the patient are the ones corresponding to the visible light ray components of solar rays not containing ultraviolet rays and infrared rays as mentioned above. Thereby, it is possible to administer medical treatment without any harmful effects caused by ultraviolet or infrared rays.

However, the afore-mentioned light ray radiation device for use in medical treatment is employed mainly for the purpose of directing the light rays onto the surface of the patient's skin. In the case of focusing the light rays onto the gums or the like in order to treat pyorrhea, gingivitis, alveolaris, etc., it is impossible to radiate the light rays effectively onto the gums by the use of the above-mentioned conventional light ray radiation device. Consequently, the favorable effect of the medical treatment cannot be obtained.

The present invention was made in consideration of the circumstances mentioned above, in particular, to provide a light ray radiation tool for use in the medical treatment of diseased gums and which radiates the light rays onto the gums directly.

Figure 2:
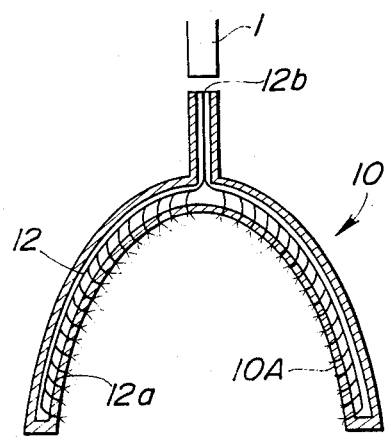
FIGS. 2 and 3 are plan cross-sectional views for explaining an embodiment of the light ray radiation tool for medical treatment of gums according to the present invention.

FIG. 2 is a plan cross-sectional view showing an embodiment of a light ray radiation tool for use in the medical treatment of diseased gums according to the present invention. In FIG. 2, 1 is an optical conductor cable through which solar rays are transmitted in the way mentioned before, and 10 is a mouthpiece, that is, a light ray radiation tool for use in the medical treatment of gums which is employed in connection with the optical conductor cable 1. The surface 10A of the mouthpiece 10 to be placed opposite to the gums is curved so as to fit against the gums, and a large number of optical fibers 12 are imbedded in the mouthpiece 10.

The end portions 12a of those optical fibers 12 are arranged respectively over the entire area of the curved surface 10A of the mouthpiece 10. The respective end portions 12a project the light rays with a projection angle equal to 90° (or near to 90°) in relation to the curved surface 10A so as to project the light rays uniformly, and the same are fixedly attached to the curved surface 10A and molded or bonded by the use of an adhesive. In such a case, since the end surface of the light ray projection coincides with the curved surface 10A, the end surface thereof can be easily cleaned and therefore it is convenient for sanitary reasons in medical applications.

Another-side end portions 12b of the optical fibers 12 are connected as an undivided whole with the optical conductor cable 1. Consequently, at the time of administering medical treatment, the afore-mentioned mouthpiece 10 is connected with the optical conductor cable 1, and when the light ray radiating surface 10A of the mouthpiece 10 comes into contact with the gums, the light rays can be radiated onto the exposed gums. And further, the radiation tool shown in FIG. 2 is employed for radiating the light rays onto the exposed gums. However, it can be used for both the lower gums and the upper gums by turning it around.

Figure 3:
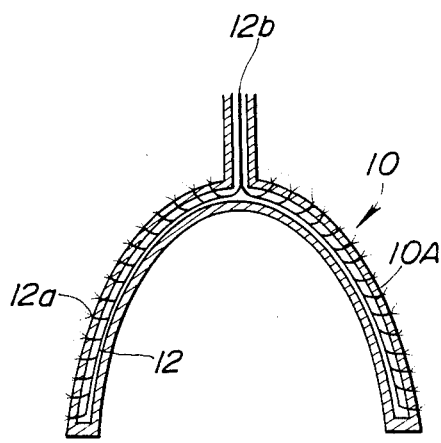

FIG. 3 is a plan cross-sectional view showing an embodiment of the light ray radiation tool for use in the medical treatment of diseased gums according to the present invention. On this occasion, the light ray radiating surface 10A is turned in a direction opposite to that of the light ray radiating surface 10A shown in FIG. 2.

Figure 4:
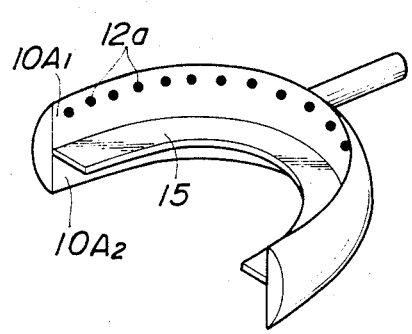
FIG. 4, FIG. 5 and FIG. 6b are perspective views, respectively, for explaining other embodiments thereof; in particular.

FIG. 4 is a perspective view showing an embodiment of the light ray radiation tool for radiating the light rays onto both of upper gums and the lower gums at the same time. On this occasion, for instance, the surface 10A radiates the light rays onto the upper external-side of the gums while the surface $10A_2$ radiates onto the lower external-side of the gums. Moreover, in FIG. 4, 15 is a biting plate and the light ray radiation tool for medical treatment of gums is stably supported by closing the teeth in on the biting plate 15.

Figure 5:
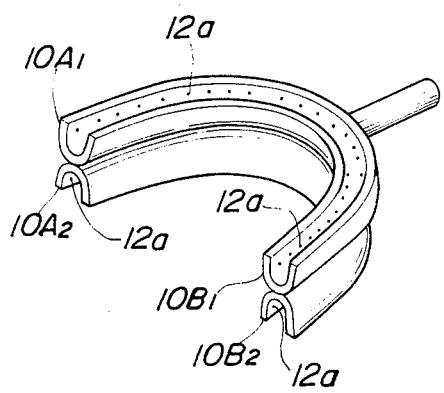

FIG. 5 is a perspective view showing an embodiment of the light ray radiation tool for radiating light rays onto all the upper and lower external-sides of the gums and the upper and lower internal-side of the gums at the same time. On this occasion, the surfaces 10A, $10A_2$ can radiate the right rays respectively onto the upper and lower external-sides of the gums while the surfaces $10B_1$ and $10B_2$ can radiate the light rays respectively onto the upper and lower internal-sides of the gums.

Figure 6A:
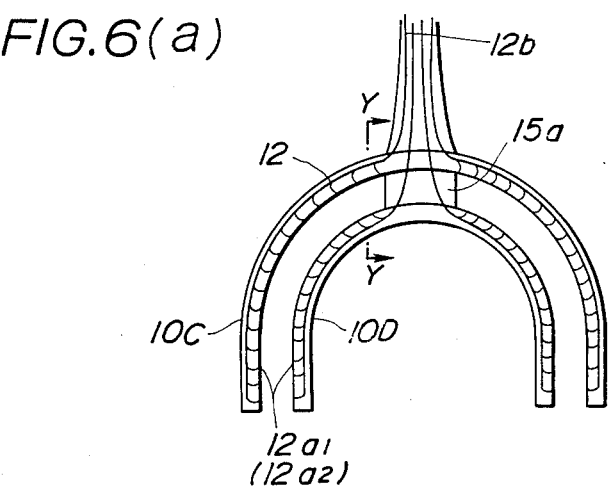
FIG. 6a is a plan cross-sectional view showing the other embodiment of the light ray radiation tool.
Figure 6B:
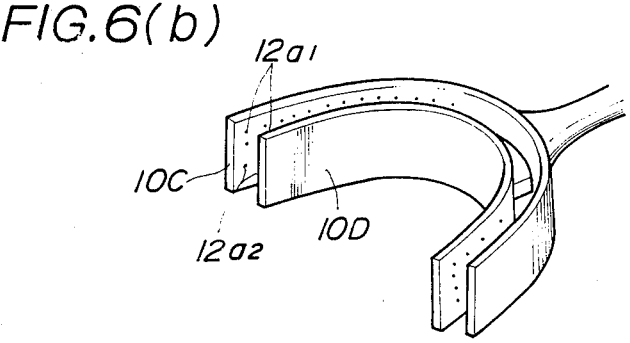
Figure 6C:
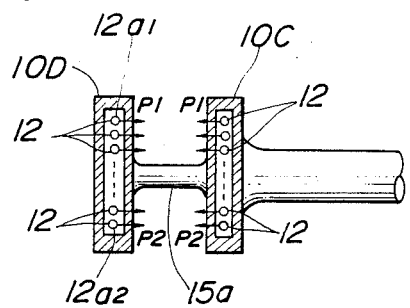

FIGS. 6a through 6c are structural views showing other embodiment of the light ray radiation tool for radiating the light rays onto all of the upper and lower external-sides of the gums and the upper and lower internal-sides of the gums at the same time as is the case in FIG. 5. FIG. 6a is a plan cross-sectional view of the same. FIG. 6b is a perspective view thereof, and FIG. 6c is a cross-sectional view taken along the line Y—Y of FIG. 6a. In those figures, the external-side mouthpiece 10c is a plate-like curved body for firmly fixing both of the end portion $12a_1$ of the optical fibers disposed in the state of a belt along the upper gums and the end portion $12a_2$ of the optical fiber disposed in a state of a belt along the lower gums at an interval corresponding to the distance between the upper and lower gums. On the contrary, the internal-side mouthpiece 10D is employed for radiating the light rays onto the upper and lower internal-side of the gums. The mouthpiece 10D is a plate-like curved body placed at the internal side of the external-side mouthpiece 10C at a uniformly-spaced interval for firmly fixing the end portions $12a_1$ and $12a_2$ of the optical fibers in the state of a belt along each of the upper and lower gums at an interval corresponding to the distance between them.

The afore-mentioned external-side and internal-side mouthpieces 10C and 10D are unitarily combined with each other by means of a plate-like biting plate 15a at the central portion thereof. The biting plate 15a has a length corresponding to the partial length of the mouthpiece 10 as compared with the whole length thereof, as shown in FIG. 6. However, the length thereof is not limited to the length as mentioned above in particular. After all, it is preferable that the biting plate 15a support the mouthpiece 10 stably and without causing any fatigue. Moreover, the solar rays radiated from the end portions $12a_1$ and $12a_2$ of the optical fibers are turned in a direction perpendicular to each of the gums as shown by the arrows $P_1$, $P_1$ and the arrows $P_2$, $P_2$ in FIG. 6c.

As is apparent from the foregoing description, according to the present invention, light rays can be radiated onto the gums effectively and simply for the purpose of administering medical treatment.

I claim:

1. A light ray radiation device for administering oral medical treatment to a person's gums comprising an optical conductor cable for conducting light rays corresponding to the visible light ray component of solar rays, a mouthpiece which receives said conducted light rays and adapted to be accommodated within a person's mouth, said mouthpiece comprising a generally curved, U-shaped structure means which conforms generally to the configuration of a person's gums, said structure means being made of a transparent material, said structure means having facing surfaces which face a person's gums when said mouthpiece is placed in a person's mouth, a plurality of optical fibers attached to said structure means, each of said optical fibers being connected to said optical conductor cable and receiving said light rays conducted by said optical cable, said plurality of optical fibers each having end portions distributed throughout said facing structure of said structure means, said end portions having end faces coincident with said facing surfaces of said structure means, said end portions projecting said light rays at an approximately right angle relative to said facing surfaces so as to project light rays conducted by said optical fibers onto a person's gums.

2. A light ray radiation device according to claim 1, further comprising adhesive means adhesively adhering said optical fibers to said structure means.

3. A light ray radiation device according to claim 1, wherein said optical fibers are molded to said structure means.

4. A light ray radiation device according to claim 3, wherein said U-shaped structure means has an outside-facing surface facing the internal surface of a person's gums, said end portions being distributed on said outside-facing surface.

5. A light ray radiation device according to claim 1, wherein said U-shaped structure has an inside-facing surface facing the external surface of a person's gums, said end portions being distributed on said inside-facing surface.

6. A light ray radiation device according to claim 1, wherein said structure means has an upper part juxtaposed to a person's upper gums and a lower part juxtaposed to a person's lower gums, said structure means further having an inner projecting bite plate between said upper and lower parts.

7. A light ray radiation device according to claim 1, wherein said structure means has an upper part with a generally U-shaped configuration juxtaposed to the internal and external surfaces of a person's upper gums, said structure means also having a lower part with an inverted generally U-shaped configuration juxtaposed to the internal and external surfaces of a person's lower gums.

8. A light ray radiation device according to claim 1, wherein said structure means comprises two spaced plate-like curved bodies, each having a generally U-shaped configuration and a bite plate connecting said spaced plate-like bodies, upper portions of said spaced plate-like curved bodies being juxtaposed to the internal and external surfaces of a person's upper gums, lower portions of said spaced plate-like curved bodies being juxtaposed to the internal and external surfaces of a person's lower gums, said bite plate being connected to said spaced plate-like bodies at an intermediate position of said spaced plate-like bodies between said upper and lower portions of said spaced plate-like bodies.

* * * * *